United States Patent
Seo et al.

(10) Patent No.: US 11,952,345 B2
(45) Date of Patent: Apr. 9, 2024

(54) METHOD FOR PREPARING BIPYRIDINE

(71) Applicants: HYUNDAI MOTOR COMPANY, Seoul (KR); KIA CORPORATION, Seoul (KR); KOREA RESEARCH INSTITUTE OF CHEMICAL TECHNOLOGY, Daejeon (KR)

(72) Inventors: Jihui Seo, Ulsan (KR); Jaeyong Lee, Seongnam-si (KR); Pyung Soon Kim, Suwon-si (KR); Jin Woo Choung, Suwon-si (KR); Yongwoo Kim, Gunpo-si (KR); Ji Hoon Park, Daejeon (KR); Soo Min Kim, Daejeon (KR); Jeong Jae Lee, Daejeon (KR); Kwanyong Jeong, Daejeon (KR)

(73) Assignees: HYUNDAI MOTOR COMPANY, Seoul (KR); KIA CORPORATION, Seoul (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 17/892,212

(22) Filed: Aug. 22, 2022

(65) Prior Publication Data

US 2023/0295090 A1   Sep. 21, 2023

(51) Int. Cl.
*C07D 213/53*   (2006.01)

(52) U.S. Cl.
CPC .................................. *C07D 213/53* (2013.01)

(58) Field of Classification Search
CPC ...................................................... C07D 213/53
See application file for complete search history.

(56) References Cited

PUBLICATIONS

Abboud, J Org Chem, 2010, 75, 3224-3231. (Year: 2010).*
Wang, Chem Asian J, 2016, 11, 2103-2106. (Year: 2016).*
Fr. Hein, et al. "A new method for the synthesis of a,a'-dipyridyl." Ber. Dtsch. Chem. Ges. A/B 61 (1928), 1790, pp. 3.
Robo, Michael T., et al. "4,4',4"-Trimethyl-2,2':6',2"-Terpyridine by Oxidative Coupling of 4-Picoline." The Journal of Organic Chemistry, vol. 79, No. 21, 2014, pp. 10624-28. Crossref, https://doi.org/10.1021/jo501925s.

* cited by examiner

*Primary Examiner* — D Margaret M Seaman
(74) *Attorney, Agent, or Firm* — Lempia Summerfield Katz LLC (57) ABSTRACT

Provided is a method for synthesizing bipyridine that includes performing a dimerization reaction of a reactant including a piperidine-based compound, a pyridine-based compound, or a mixture thereof in the presence of a catalyst in which an active metal is supported on a composite metal oxide support including silica ($SiO_2$) and alumina ($Al_2O_3$).

15 Claims, 7 Drawing Sheets

METHOD FOR PREPARING BIPYRIDINE

CROSS-REFERENCE TO RELATED APPLICATION

This application claims priority to and the benefit of Korean Patent Application No. 10-2022-0031800 filed in the Korean Intellectual Property Office on Mar. 15, 2022, the entire contents of which are incorporated herein by reference.

BACKGROUND

(a) Field

The present disclosure relates to a method for inexpensively synthesizing bipyridine, which can be utilized as a hydrogen storage medium through pure catalysis.

(b) Description of the Related Art

The statements in this section merely provide background information related to the present disclosure and may not constitute prior art.

Since bipyridine is mainly used as a ligand, regioselectivity of N-hetero atoms is important. However, in order to impart the regioselectivity to the N-hetero atoms during the bipyridine synthesis, the bipyridine synthesis requires a high cost.

For example, a general method for preparing the bipyridine uses a high-priced material such as halopyridine as a reactant, which requires a purification process.

For another example, a method of synthesizing the bipyridine uses a dimerization reaction of pyridine rather than the halopyridine and requires a high temperature of about 300° C. or higher or an oxidant to cut off hydrogens.

Accordingly, we have discovered that a method of synthesizing the bipyridine through the dimerization reaction without the oxidant at a low temperature and also at a low cost is desired.

SUMMARY

The present disclosure provides a method of synthesizing bipyridine. The method does not require an oxidant or a high temperature of about 300° C. or higher for cutting off hydrogens and also, does not use a high cost reactant such as halopyridine and thus reduces costs for synthesizing the bipyridine.

According to one aspect of the present disclosure, the method for synthesizing bipyridine includes: performing a dimerization reaction of a reactant including a piperidine-based compound, a pyridine-based compound, or a mixture thereof in the presence of a catalyst in which an active metal is supported on a composite metal oxide support including silica ($SiO_2$) and alumina ($Al_2O_3$).

In the method for synthesizing bipyridine, the piperidine-based compound may be subjected to a dehydrogenation reaction to prepare the pyridine-based compound in the presence of a catalyst, and the pyridine-based compound may be subjected to a dimerization reaction in the presence of a catalyst.

The dehydrogenation reaction and the dimerization reaction may proceed as a one-pot reaction.

The piperidine-based compound may include piperidine, 2-methylpiperidine, 3-methylpiperidine, 4-methylpiperidine, 3,4-dimethylpiperidine, 2,4-dimethylpiperidine, 2,5-dimethylpiperidine, 2,6-dimethylpiperidine, 3,5-dimethylpiperidine, or a mixture thereof.

The pyridine-based compound may include pyridine, 2-picoline, 3-picoline, 4-picoline, or a mixture thereof.

The composite metal oxide support may include silica in an amount of about 1 wt % to about 50 wt % based on the total weight of the composite metal oxide support.

The active metal may include Pd, Pt, Ru, Sn, Mn, Zn, Mg, V, Ce, La, Y, Sm, Gd, Na, K, Cs, Rb, Ni, Rh, Ir, Co, Fe, Cr, Cu, or a mixture thereof.

The catalyst may include an active metal in an amount of about 0.1 wt % to about 10 wt % based on the total weight of the catalyst.

The catalyst may further include an auxiliary metal other than the active metal in an amount of about 1 wt % to about 20 wt % based on the total weight of the catalyst.

The catalyst may be present in an amount of about 0.3 mole to about 1.0 mole of the active metal of the catalyst based on 100 moles of the reactant.

The dehydrogenation reaction, the dimerization reaction, or both may proceed at about 150° C. to about 250° C.

The dehydrogenation reaction, the dimerization reaction, or both may proceed at about 1 $bar_g$ to about 5 $bar_g$.

After mixing an acid with the reactant, the dimerization reaction may be performed.

The acid may include sulfuric acid, nitric acid, phosphoric acid, hydrochloric acid, boric acid, heteropolyacid, acetic acid, formic acid, malic acid, citric acid, tartaric acid, ascorbic acid, lactic acid, oxalic acid, succinic acid, tauric acid, or a mixture thereof.

The acid may be mixed in an amount of about 0.001 mole to about 0.05 mole based on 100 moles of the reactant.

Unlike a conventional method using halopyridine and thus requiring a higher cost, the method for synthesizing bipyridine according to one aspect of the present disclosure does not require an oxidant or a high temperature of about 300° C. or higher for cutting off hydrogens and uses a pure dimerization reaction at a much lower cost, and thus may increase availability of the bipyridine as a hydrogen storage medium.

BRIEF DESCRIPTION OF THE DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The advantages and features of the present disclosure and the methods for accomplishing the same should be apparent from the embodiments described hereinafter. However, the embodiments should not be construed as being limited to the embodiments set forth herein. Unless otherwise defined, all terms (including technical and scientific terms) used herein have the same meaning as commonly understood by one of ordinary skill in the art. The terms defined in a generally-used dictionary may not be interpreted ideally or exaggeratedly unless clearly defined.

In addition, unless explicitly described to the contrary, the word "comprise," and variations such as "comprises" or "comprising," should be understood to imply the inclusion of stated elements but not the exclusion of any other elements. Further, the singular includes the plural unless mentioned otherwise. When a component, device, element, or the like of the present disclosure is described as having a purpose or performing an operation, function, or the like, the component, device, or element should be considered herein as being "configured to" meet that purpose or to perform that operation or function.

According to one aspect of the present disclosure, a method for synthesizing bipyridine includes: performing a dimerization reaction of a reactant in the presence of a catalyst to synthesize bipyridine.

The reactant may include a piperidine-based compound, a pyridine-based compound, or a mixture thereof.

The piperidine-based compound may be piperidine or piperidine substituted with one or more alkyl groups. The alkyl group may be an alkyl group having 1 to 10 carbon atoms, or a methyl group. The piperidine substituted with one or more alkyl groups may be -methylpiperidine, 3-methylpiperidine, 4-methylpiperidine, 3,4-dimethylpiperidine, 2,4-dimethylpiperidine, 2,5-dimethylpiperidine, 2,6-dimethylpiperidine, 3,5-dimethylpiperidine, or a mixture thereof, for example 2-methylpiperidine or 2,6-dimethylpiperidine.

The pyridine-based compound may be pyridine or pyridine substituted with one or more alkyl groups. The alkyl group may be an alkyl group having 1 to 10 carbon atoms, or a methyl group. The pyridine substituted with one or more alkyl groups may include 2-picoline, 3-picoline, 4-picoline, or a mixture thereof.

The catalyst may include an active metal supported on a composite metal oxide support.

The composite metal oxide support includes silica ($SiO_2$) and alumina ($Al_2O_3$).

The alumina may include $\theta$-$Al_2O_3$, $\gamma$-$Al_2O_3$, $\alpha$-$Al_2O_3$, $\eta$-$Al_2O_3$, $\delta$-$Al_2O_3$, $\kappa$-$Al_2O_3$, or a mixture thereof.

The composite metal oxide support may include silica in an amount of about 1 wt % to about 50 wt %, for example about 1 wt % to about 10 wt % based on the total weight of the composite metal oxide support. When the silica content in the metal oxide support is less than about 1 wt %, acidity controlling role of the support by the added silica may not be properly exhibited. When the silica content in the metal oxide support exceeds about 50 wt %, a surface area and pore size of the composite metal oxide may be reduced.

In addition, the composite metal oxide support may further include $Pr_2O_3$, MgO, $ZrO_2$, $CeO_2$, $La_2O_3$, $SiO_2$, or a mixture thereof. The composite metal oxide support may include an additional metal oxide in an amount of about 1 wt % to about 50 wt % based on the total weight of the composite metal oxide support.

The composite metal oxide support may have a binary pore size distribution including meso pores with an average pore size of about 5 nm to about 100 nm and macro pores with an average pore size of about 0.1 μm to about 20 μm. Because of this binary pore size distribution, the catalyst may improve activity and ease of regeneration in the dehydrogenation reaction. When the pore size of the support is less than 5 nm, a mass transfer rate may be deteriorated, but when the pore size is greater than 20 μm, strength of the support may be deteriorated. In other words, when the pore size is in a range of about 10 nm to about 1000 nm, the catalyst may have transition diffusion, when the pore size is about 1000 nm or larger, the catalyst may have bulk diffusion. Accordingly, when the support has macro pores of about 1 μm or more, the mass transfer rate may be about 20 times or higher than when the support has pores of about 10 nm.

The composite metal oxide support may have a specific surface area of about 55 $m^2$/g to about 140 $m^2$/g. When the specific surface area of the support is less than about 55 $m^2$/g, a dispersion degree of the active metal and auxiliary metal may be low, and when it exceeds about 140 $m^2$/g, side reactivity may increase.

The composite metal oxide support may have a strength of about 20 N to about 50 N. When the strength of the support is increased, the catalyst may be inhibited or prevented from crumbling of even during the regeneration or circulation of the catalyst. When the strength of the support is less than about 20 N, the support may be easily cracked and thus difficult to apply to a continuous reaction system and also, easily undergo thermal cracking during the regeneration process. In addition, because the catalyst experiences friction or impact during the transport, while circulated and operated in the dehydrogenation reaction, a weak support to the impact may impede a flow of products and increase a pressure in the reactor and thereby, lower a conversion rate of the catalyst. Thus, the support should have high strength to secure huge advantages during the process operation.

The active metal is a component that has activity during the dimerization reaction of a reactant and is supported on a support. For example, the active metal may further include Pd, Pt, Ru, Sn, Mn, Zn, Mg, V, Ce, La, Y, Sm, Gd, Na, K, Cs, Rb, Ni, Rh, Ir, Co, Fe, Cr, Cu, or a mixture thereof.

The catalyst may include about 0.1 wt % to about 10 wt %, for example, 0.5 wt % to 10 wt % of the active metal, based on the total weight of the catalyst. When the active metal content is less than about 0.1 wt %, the activity of the dimerization reaction may be reduced. When the active metal content exceeds about 10 wt %, the activity of the catalyst may be reduced due to a decrease in the dispersion degree of the active metal.

The catalyst may further include an auxiliary metal other than the active metal. The auxiliary metal may be further included in an amount of about 1 wt % to about 20 wt % based on the total weight of the catalyst.

The auxiliary metal may further include Pd, Pt, Ru, Sn, Mn, Zn, Mg, V, Ce, La, Y, Sm, Gd, Na, K, Cs, Rb, Ni, Rh, Ir, Co, Fe, Cr, Cu, or a mixture thereof. For example, when the active metal is Pd, Pt may be further included as an auxiliary metal.

The catalyst may be present in an amount of about 0.3 mole to about 10 moles, for example, about 0.5 mole to about 2 moles of the active metal of the catalyst based on 100 moles of the reactant. When the active metal of the catalyst is present in an amount of less than about 0.3 mole based on 100 moles of the reactant, the amount of the active metal is significantly small, compared with that of the reactant, lowering the reaction rate. However, when the active metal of the catalyst is present in an amount of greater than about 10 moles, a total amount of the catalyst on which the active metal is supported relative to that of the reactant may be excessive, increasing viscosity of the mixture and thus making it difficult to operate the reactor.

In the method of synthesizing bipyridine, only the dimerization reaction of the reactants may be performed, and the dimerization reaction may be continuously performed following the dehydrogenation reaction of the reactant.

Figure 1:
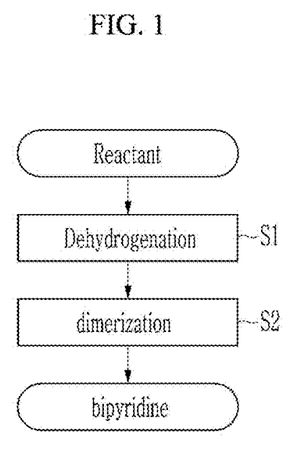
FIG. 1 is a process flow chart showing a method for synthesizing bipyridine according to an aspect of the present disclosure.

FIG. 1 is a process flow chart showing a method for synthesizing bipyridine in the case that the dimerization reaction is continuously performed following the dehydrogenation reaction.

Referring to FIG. 1, the piperidine-based compound is subjected to dehydrogenation in the presence of a catalyst to prepare a pyridine-based compound (S1), and the pyridine-based compound is subjected to dimerization in the presence of a catalyst to synthesize bipyridine (S2).

For example, when the reactant is 2-methylpiperidine, the reaction shown in Reaction Scheme 1 may proceed.

[Reaction Scheme 1]

The dehydrogenation reaction and the dimerization reaction may proceed under the same catalyst, and when the catalyst includes the composite metal oxide support including silica and alumina, the dehydrogenation reaction and the dimerization reaction may proceed at once. Accordingly, the catalyst including the composite metal oxide support including silica and alumina may be used to proceed the dehydrogenation reaction and the dimerization reaction as one-pot reaction.

In addition, in the method of synthesizing bipyridine, the dimerization reaction may be performed after mixing the reactant and the acid. The acid may act as oxidants to improve reaction activity.

The acid may include sulfuric acid, nitric acid, phosphoric acid, hydrochloric acid, boric acid, heteropolyacid, acetic acid, formic acid, malic acid, citric acid, tartaric acid, ascorbic acid, lactic acid, oxalic acid, succinic acid, tauric acid, or a mixture thereof, and the acid may be for example formic acid.

The acid may be mixed in an amount of about 0.001 mole to about 0.05 mole, for example about 0.003 mole to about 0.01 mole based on 100 moles of the reactant. When the acid content is less than about 0.001 mole, reactivity due to the addition of the acid may not be improved. When the acid content exceeds about 0.05 mole, a yield of the dimerization product may decrease due to the formation of a salt between the reactant and the acid.

The dehydrogenation reaction, the dimerization reaction, or both may be performed at a low temperature of about 150° C. to about 250° C., for example, about 170° C. to about 200° C. When the reaction temperature is less than about 150° C., energy required for the two reactions may not be supplied, and thus the reaction rate and yield may be lowered, and when it exceeds about 250° C., unwanted side reactions may occur.

The dehydrogenation reaction, the dimerization reaction, or both may proceed at about 1 $bar_g$ to about 5 $bar_g$, for example about 1 $bar_g$ to about 3 $bar_g$.

When the reaction pressure is less than about 1 $bar_g$, the reactant has a lower boiling point than the reaction temperature under a low pressure and thus, may be all gasified, and when the reaction pressure is greater than about 5 $bar_g$, since the two reactions are reversible reactions that generate gas, a high pressure may rather activate a reverse reaction.

Hereinafter, specific examples of the present disclosure are described. However, the examples described below are for illustrative purposes only, and the scope of the present disclosure is not limited thereto.

Preparation Example: Preparation of Catalyst

Preparation Example 1: Pd/SiO$_2$—Al$_2$O$_3$

An SiO$_2$—Al$_2$O$_3$ composite metal oxide was prepared in a solvent-deficient precipitation method. Specifically, tetraethyl orthosilicate, a silica precursor, and aluminum nitrate nonahydrate, an alumina precursor, were prepared in a weight ratio of SiO$_2$:Al$_2$O$_3$=1:99. In addition, 3 equivalents of ammonium bicarbonate for the two precursors was prepared.

Subsequently, each material was put in a mortar and stirred with a pestle at room temperature. Each precursor was dissolved by hydrated water, and the ammonium bicarbonate was decomposed, generating CO$_2$. The stirring was kept for 20 minutes, until the ammonium bicarbonate was all decomposed and thus generated no CO$_2$. Subsequently, SiO$_2$—Al$_2$O$_3$ composite metal oxide was obtained by baking at 600° C. for 5 hours.

On the other hand, palladium (II) nitrate hydrate (Pd(NO$_3$)$_2$·xH$_2$O) as a palladium (Pd) precursor was weighed to have 5 wt % of palladium and then, dissolved in distilled water to prepare a precursor solution, and the SiO$_2$—Al$_2$O$_3$ composite metal oxide in a powder state was added thereto and then, stirred. The resultant was dried at 100° C. for about 12 hours by evaporating water to support the palladium on the SiO$_2$—Al$_2$O$_3$ composite metal oxide.

Experimental Example 1

Figure 2:
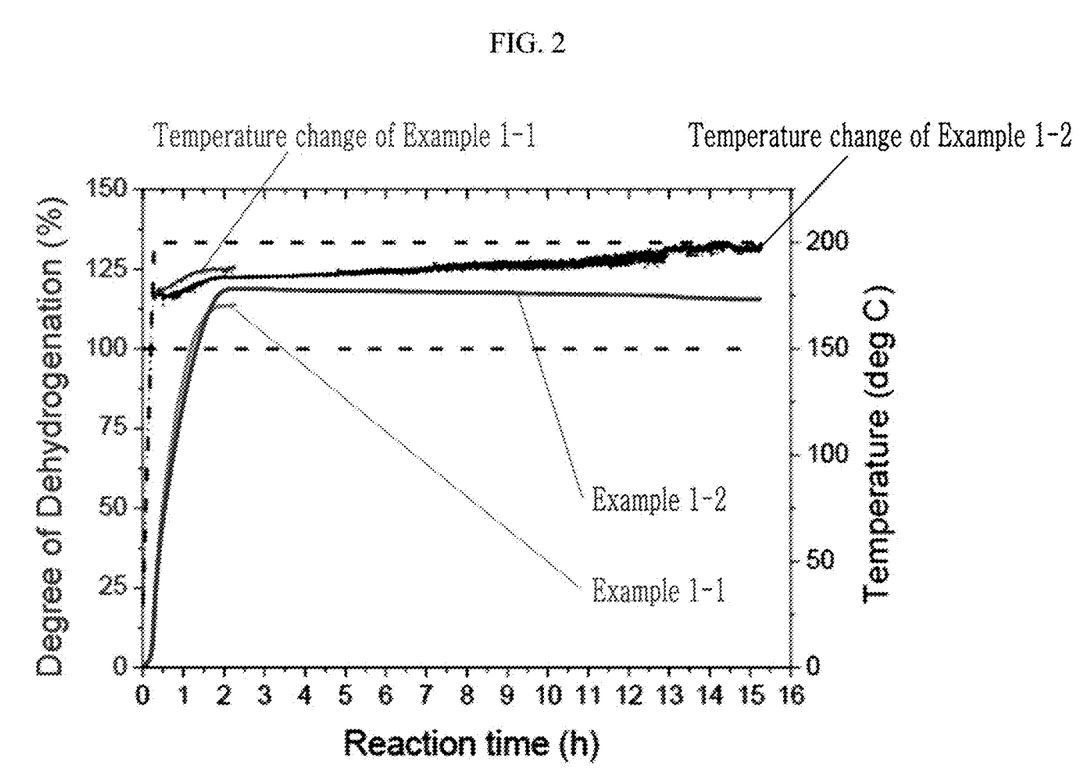
FIG. 2 is a graph showing the result of the dehydrogenation reaction of 2-methylpyridine in Experimental Example 1.
Figure 3:
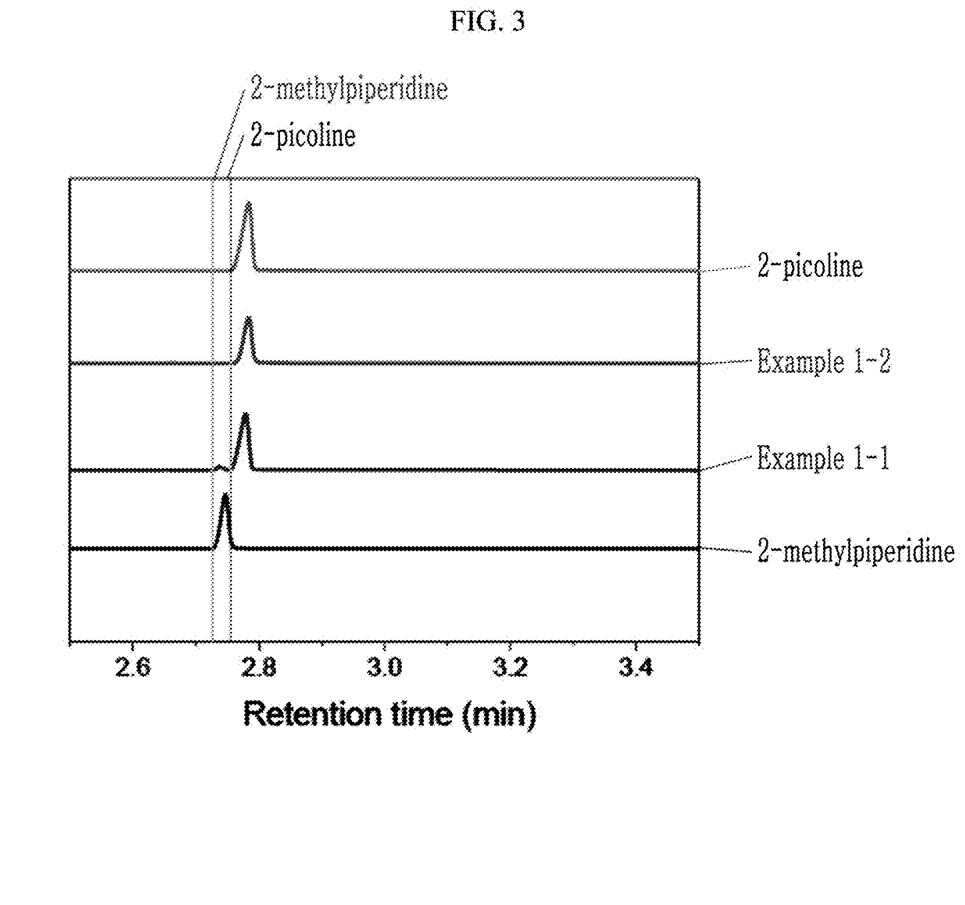
FIG. 3 is a graph showing a material produced as a result of the dehydrogenation reaction of 2-methylpyridine in Experimental Example 1.
Figure 4:
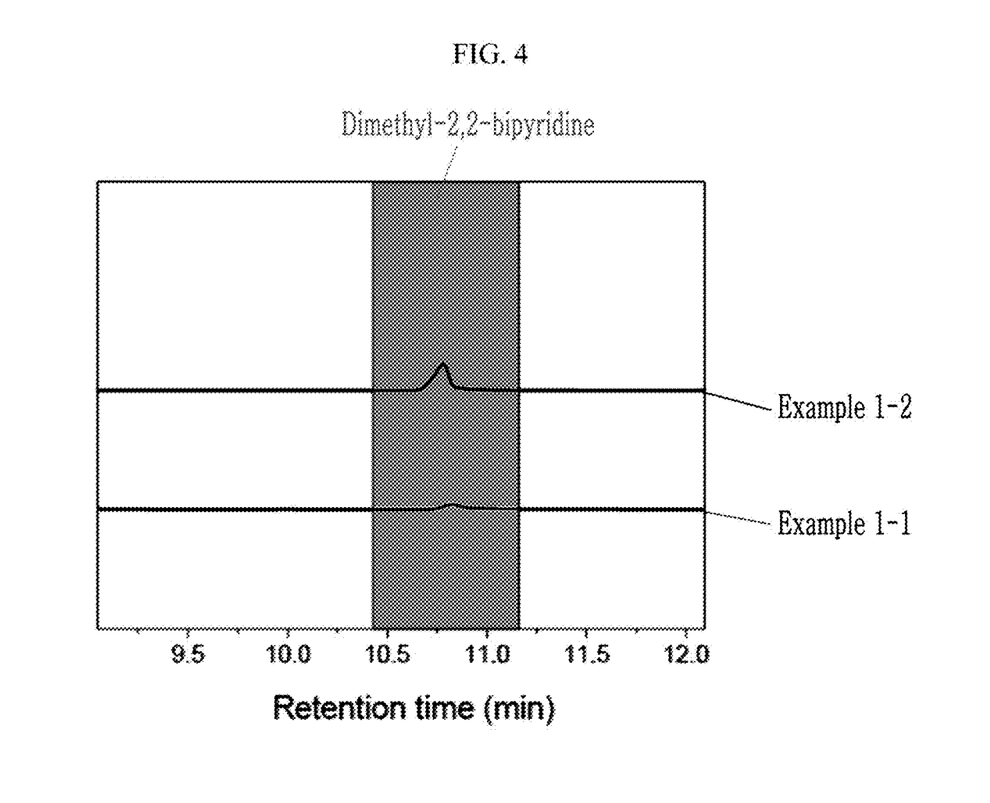
FIG. 4 is a graph showing a material produced as a result of the dimerization reaction of 2-methylpyridine in Experimental Example 1.

2-methylpyridine as a reactant was reacted under the catalyst of Preparation Example at 200° C. under a pressure of 3 $bar_g$ under a condition of using 1 mol of metal based on 100 moles of the reactant catalyst, and the results are shown in FIGS. 2 to 4.

FIG. 2 is a graph showing the result of the dehydrogenation reaction, FIG. 3 is a graph showing the material produced as a result of the dehydrogenation reaction, and FIG. 4 is a graph showing the material produced as a result of the dimerization reaction.

In FIGS. 2 to 4, in Example 1-1, a reaction was carried out for 2 hours, producing 47.31 mmol of $H_2$ and exhibiting dehydrogenation activity of 94.15%, and a product therefrom had 3.94 wt % of 2-methylpiperidine, 91.45 wt % of 2-picoline, and 4.61 wt % of dimethyl-2,2-bipyridine (Retention time: 10.82 min). In Example 1-2, a reaction was carried out for 15 hours, producing 48.04 mmol of $H_2$ and exhibiting dehydrogenation activity of 95.91%, and a product therefrom had 2-0 wt % of methylpiperidine, 82.57 wt % of 2-picoline, and 17.43 wt % of dimethyl-2,2-bipyridine (Retention time: 10.78 min).

Referring to FIGS. 2 to 4, when 2-methylpiperidine was reacted with a $Pd/SiO_2$—$Al_2O_3$ catalyst, a primary product of 2-picoline was dimerized, synthesizing dimethyl-2,2-bipyridine. In other words, one type of catalyst was used for both dehydrogenation and dimerization reactions, and as reaction time increased, a yield of bipyridine also increased.

Experimental Example 2

Synthesis yield changes of bipyridine according to reaction time and a type of reactant were measured. A reaction was equally performed as in Experimental Example 1, but the reaction time was changed as shown in Table 1, and the type of reactant was changed as shown in Table 2.

TABLE 1

|  | Reactant | Reaction time (hour) | Dimerization yield (%) |
|---|---|---|---|
| Example 2-1 | 2-methylpiperidine | 2 | 3.141 |
| Example 2-2 | 2-methylpiperidine | 6 | 7.166 |
| Example 2-3 | 2-methylpiperidine | 15 | 14.257 |
| Example 2-4 | 2-picoline | 2 | 5.017 |
| Example 2-5 | 2-picoline | 6 | 13.108 |
| Example 2-6 | 2-picoline | 60 | 24.791 |

TABLE 2

|  | Reactant | Reaction time (hour) | Dimerization yield (%) |
|---|---|---|---|
| Example 2-7 | 2-picoline + pyridine | 2 | 4.850 |
| Example 2-8 | 4-picoline + pyridine | 2 | 8.706 |
| Example 2-9 | 2-picoline + 4-picoline | 2 | 8.779 |

Referring to Table 1, as the reaction time increased, as the yield increased, wherein when the reaction time was 60 hours, the dimerization yield was 24.79%.

Referring to Table 2, when 4-picoline was mixed as a reactant of the dimerization reaction, the bipyridine synthesis yield increased to 8.78%. Accordingly, when the 4-picoline was used as a reactant, the yield was improved by almost 2 times.

For reference, the number or positions of methyl groups in the synthesized bipyridine may vary depending on a type of reactant, but when the bipyridine is used as not a ligand but a hydrogen storage medium, regioselectivity of the methyl groups is not greatly important. In other words, bipyridine mixtures having different positions and number of methyl groups and pure 2,2-bipyridine had no large difference in hydrogenation and dehydrogenation reactivity, and the bipyridine mixtures having different positions and number of methyl groups had an advantage of rather maintaining a liquid phase.

Experimental Example 3

Synthesis yield changes of bipyridine depending on a type of support of a catalyst were measured. A reaction was equally carried out as in Experimental Example 1, but in FIG. 5, the reaction was carried by changing a content of silica, and in FIGS. 6 and 7, the reaction was carried out by using zeolite (zeolite Y catalyst: CBV 300, S/Al mole ratio=5:1, Pore volume: 0.301 $cm^3/g$) as a support of a catalyst (Comparative Example 1).

Figure 5:
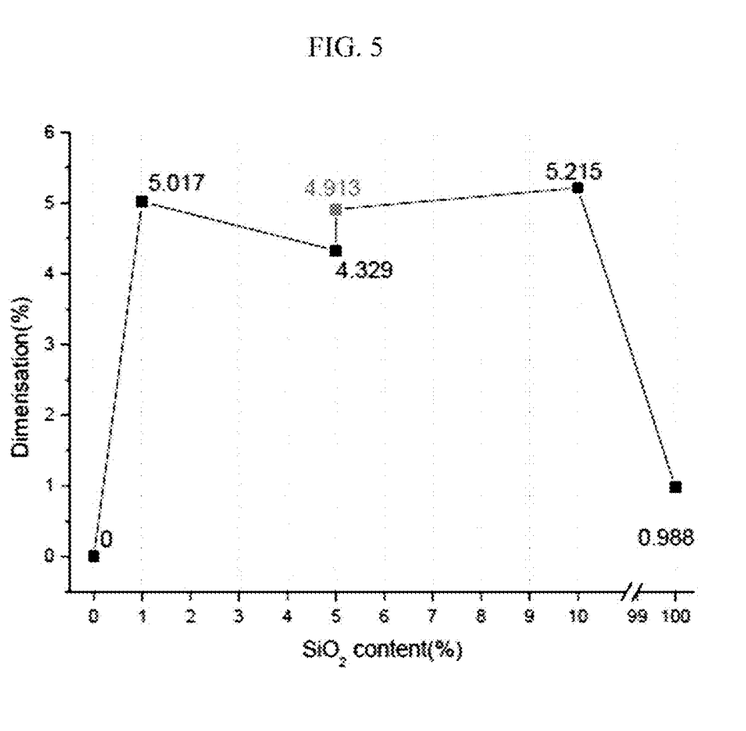
FIG. 5 is a graph showing the dimerization reaction yield according to the content of silica in the composite metal oxide support in Experimental Example 2.

Referring to FIG. 5, in $Pd/SiO_2$ having 100 wt % of a silica content and $Pd/Al_2O_3$ having 0 wt % of a silica content, the bipyridine was not almost synthesized, but when silica and alumina were appropriately mixed, dimerization activity was secured, and when the silica was included within a range of 1 wt % to 10 wt %, the dimerization activity exhibited no significant change.

Figure 6:
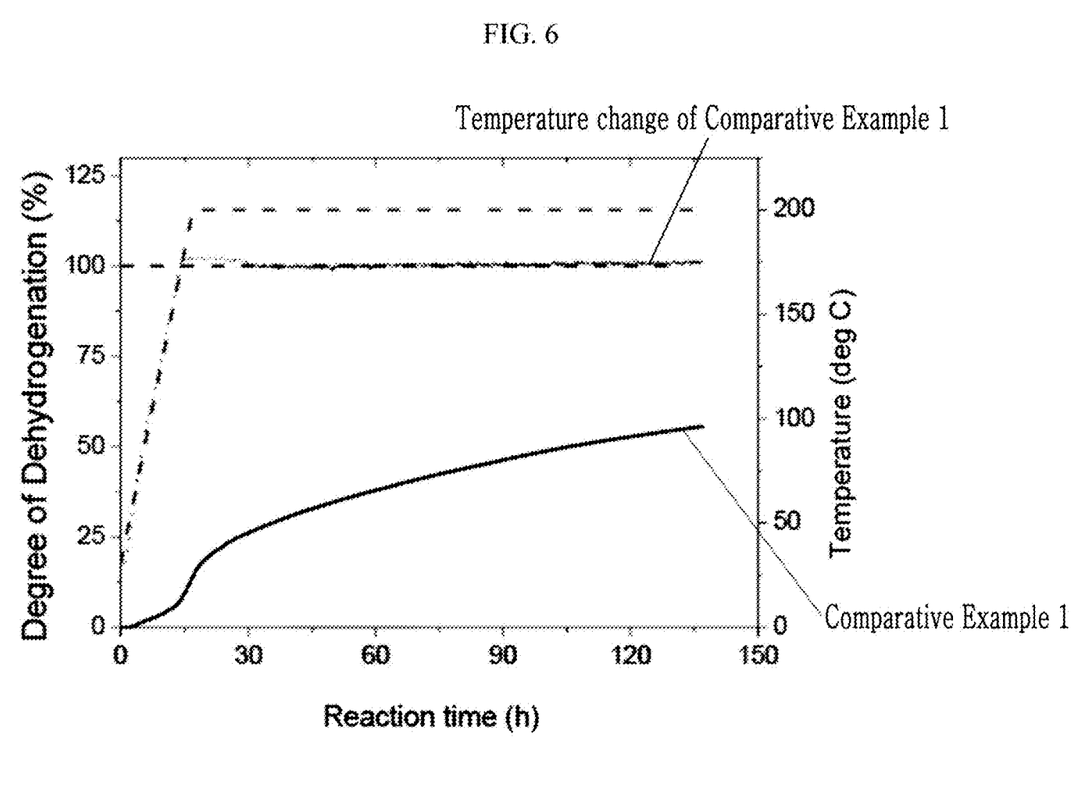
FIG. 6 is a graph showing the results of the dehydrogenation reaction according to the type of support in Experimental Example 2.
Figure 7:
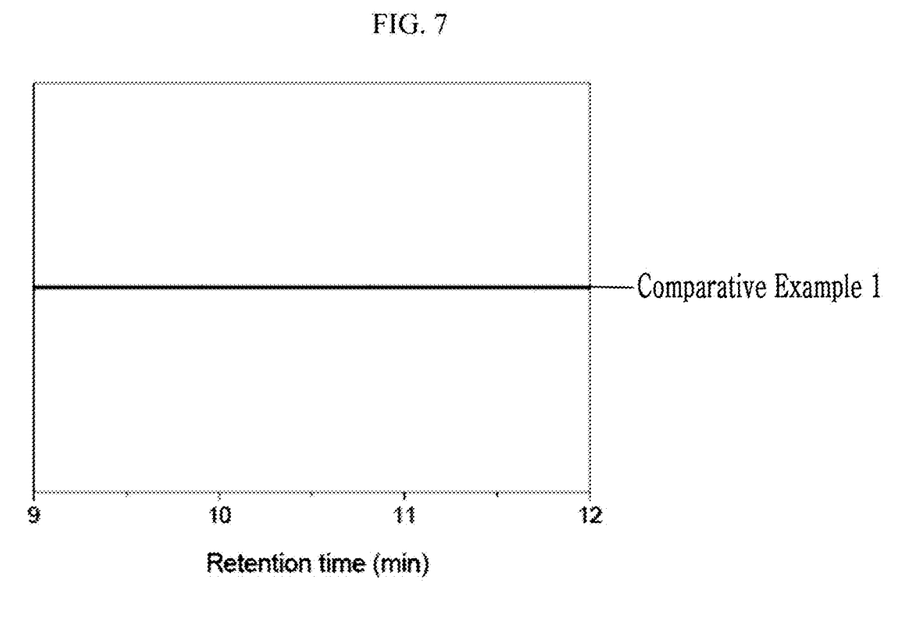
FIG. 7 is a graph showing a material produced as a result of a dimerization reaction according to the type of support in Experimental Example 2.

Referring to FIGS. 6 and 7, when a zeolite catalyst was used, there was no dimerization activity at all, and dehydrogenation reactivity of 2-methylpiperidine also dropped to 23.13 mmol $H_2$, 55.62%.

Experimental Example 4

Synthesis yield changes of bipyridine according to addition of acid to a reactant were measured. A reaction was equally carried out as in Experimental Example 1, but an amount of the acid was changed as shown in Table 3.

TABLE 3

|  | Reactant |  | Catalyst | M/R | Acetic acid | Reaction condition | | | |
|---|---|---|---|---|---|---|---|---|---|
|  |  |  |  |  |  | Temperature | Pressure | Time | Yield |
| Comp. Ex. 2 | benzene | 200 mg | 3.8 wt % Pd(II)@GO | 0.3 | 6.8 eq | 80° C. | 1 $bar_g$ $O_2$ | 12 h | 78% |
| Ex. 3-1 | 2-picoline | 1.2912 g | 5 wt % $Pd/SiO_2$-$Al_2O_3$ | 1 | None | 200° C. | 3 $bar_g$ Ar | 15 h | 13.108% |
| Ex. 3-2 | 2-picoline | 3.8736 g | 5 wt % $Pd/SiO_2$-$Al_2O_3$ | 1 | None | 250° C. | Ar (the atmospheric pressure) | 15 h | 19.926% |
| Ex 3-3 | 2-picoline | 1.2912 g | 5 wt % $Pd/SiO_2$-$Al_2O_3$ | 1 | 0.033 mL | 200° C. | 3 $bar_g$ $O_2$ | 15 h | 6.922% |

TABLE 3-continued

|  | Reactant |  | Catalyst | M/R | Acetic acid | Reaction condition | | | Yield |
|---|---|---|---|---|---|---|---|---|---|
|  |  |  |  |  |  | Temperature | Pressure | Time |  |
| Ex. 3-4 | 2-picoline | 3.8736 g | 5 wt % Pd/SiO$_2$-Al$_2$O$_3$ | 1 | 0.1 mL | 250° C. | O$_2$ (the atmospheric pressure) | 15 h | 3.760% |

Referring to Table 3, as in Comparative Example 2, when acid and O$_2$ as an oxidant were added in a dimerization reaction of benzene, activity was increased. On the contrary, as shown from Example 3-1 to Example 3-4, when acetic acid was added under an O2 atmosphere in the dimerization reaction of 2-picoline, activity was rather deteriorated.

In addition, referring to Examples 3-2 and 3-3, when a pressure was reduced, but a reaction temperature was increased up to 250° C., activity was increased.

On the contrary, referring to Example 3-4, although the temperature was increased up to 250° C., when acid and O$_2$ were added, activity was much deteriorated.

While this present disclosure has been described in connection with what is presently considered to be practical example embodiments, it should be understood that the present disclosure is not limited to the disclosed embodiments. On the contrary, it is intended to cover various modifications and equivalent arrangements included within the spirit and scope of the present disclosure.

What is claimed is:

1. A method for synthesizing bipyridine, comprising:
   performing a dimerization reaction of a reactant consisting of a piperidine-based compound, a pyridine-based compound, or a mixture thereof,
   in presence of a catalyst in which an active metal is supported on a composite metal oxide support consisting of silica (SiO$_2$) and alumina (Al$_2$O$_3$).

2. The method of claim 1, wherein
   the piperidine-based compound is subjected to a dehydrogenation reaction to prepare the pyridine-based compound in the presence of a catalyst, and
   the pyridine-based compound is subjected to a dimerization reaction in the presence of a catalyst.

3. The method of claim 2, wherein the dehydrogenation reaction and the dimerization reaction proceed as a one-pot reaction.

4. The method of claim 1, wherein the piperidine-based compound consists of piperidine, 2-methylpiperidine, 3-methylpiperidine, 4-methylpiperidine, 3,4-dimethylpiperidine, 2,4-dimethylpiperidine, 2,5-dimethylpiperidine, 2,6-dimethylpiperidine, 3,5-dimethylpiperidine, or a mixture thereof.

5. The method of claim 1, wherein the pyridine-based compound consists of pyridine, 2-picoline, 3-picoline, 4-picoline, or a mixture thereof.

6. The method of claim 1, wherein the composite metal oxide support consists of silica in an amount of about 1 wt % to about 50 wt % based on a total weight of the composite metal oxide support.

7. The method of claim 1, wherein the active metal consists of Pd, Pt, Ru, Sn, Mn, Zn, Mg, V, Ce, La, Y, Sm, Gd, Na, K, Cs, Rb, Ni, Rh, Ir, Co, Fe, Cr, Cu, or a mixture thereof.

8. The method of claim 1, wherein the catalyst consists of an active metal in an amount of about 0.1 wt % to about 10 wt % based on a total weight of the catalyst.

9. The method of claim 1, wherein the catalyst consists of an auxiliary metal other than the active metal in an amount of about 1 wt % to about 20 wt % based on a total weight of the catalyst.

10. The method of claim 1, wherein the catalyst is present in an amount of about 0.3 mole to about 1.0 mole of the active metal of the catalyst based on 100 moles of the reactant.

11. The method of claim 2, wherein the dehydrogenation reaction, the dimerization reaction, or both proceed at about 150° C. to about 250° C.

12. The method of claim 2, wherein the dehydrogenation reaction, the dimerization reaction, or both proceed at about 1 bar$_g$ to about 5 bar$_g$.

13. The method of claim 1, further comprising: mixing an acid with the reactant, and then performing the dimerization reaction.

14. The method of claim 13, wherein the acid consists of sulfuric acid, nitric acid, phosphoric acid, hydrochloric acid, boric acid, heteropolyacid, acetic acid, formic acid, malic acid, citric acid, tartaric acid, ascorbic acid, lactic acid, oxalic acid, succinic acid, tauric acid, or a mixture thereof.

15. The method of claim 13, wherein the acid is mixed in an amount of about 0.001 mole to about 0.05 mole based on 100 moles of the reactant.

* * * * *

UNITED STATES PATENT AND TRADEMARK OFFICE
CERTIFICATE OF CORRECTION

PATENT NO.          : 11,952,345 B2
APPLICATION NO.     : 17/892212
DATED               : April 9, 2024
INVENTOR(S)         : Jihui Seo et al.

It is certified that error appears in the above-identified patent and that said Letters Patent is hereby corrected as shown below:

On the Title Page

Item (30) Foreign Application Priority Data please add:
March 15, 2022 (KR) ................10-2022-0031800

Signed and Sealed this
Twenty-eighth Day of May, 2024

Katherine Kelly Vidal
*Director of the United States Patent and Trademark Office*